(12) United States Patent
Smith et al.

(10) Patent No.: US 11,771,836 B2
(45) Date of Patent: *Oct. 3, 2023

(54) ASSEMBLY FOR A MEDICATION DELIVERY DEVICE AND MEDICATION DELIVERY DEVICE

(71) Applicant: NORTON HEALTHCARE LIMITED, Castleford (GB)

(72) Inventors: Christopher James Smith, Prenton (GB); Dale Marc Comley, Parchwich (GB); Lee Thomas Smith, Tixall (GB)

(73) Assignee: NORTON HEALTHCARE LIMITED, Castleford (GB)

(*) Notice: Subject to any disclaimer, the term of this patent is extended or adjusted under 35 U.S.C. 154(b) by 406 days.

This patent is subject to a terminal disclaimer.

(21) Appl. No.: 16/483,152

(22) PCT Filed: Jan. 25, 2018

(86) PCT No.: PCT/EP2018/051877
§ 371 (c)(1),
(2) Date: Aug. 2, 2019

(87) PCT Pub. No.: WO2018/141635
PCT Pub. Date: Aug. 9, 2018

(65) Prior Publication Data
US 2020/0164150 A1 May 28, 2020

(30) Foreign Application Priority Data
Feb. 3, 2017 (EP) .................................... 17154634

(51) Int. Cl.
*A61M 5/315* (2006.01)
*A61M 5/31* (2006.01)
*A61M 5/50* (2006.01)

(52) U.S. Cl.
CPC ........ *A61M 5/3155* (2013.01); *A61M 5/3146* (2013.01); *A61M 5/31528* (2013.01);
(Continued)

(58) Field of Classification Search
CPC ............ A61M 5/3146; A61M 5/31528; A61M 5/3155; A61M 5/31551; A61M 5/3158;
(Continued)

(56) References Cited

U.S. PATENT DOCUMENTS 5,226,895 A 7/1993 Harris
2006/0270985 A1 11/2006 Hommann et al.
(Continued)

FOREIGN PATENT DOCUMENTS

DE 102004045326 A1 11/2005
EP 0496141 A1 7/1992
(Continued)

*Primary Examiner* — Shefali D Patel
(74) *Attorney, Agent, or Firm* — David S. Safran; Calderon Safran & Cole P.C.

(57) ABSTRACT

An assembly (47) for a medication delivery device (1) has a body (2), a dose setting part (8) configured to be operated by a user for selecting a size of a dose, a piston rod (13) configured to be moved axially without rotating for dispensing a medication, and a drive member (12) being directly coupled to the piston rod (13) for driving the piston rod (13) in a dose dispensing operation, wherein the drive member (12) moves in a proximal direction in a dose setting operation. The medication delivery device (1) into which the assembly is incorporated may be a single-shot, variable-dose injection device, e.g., a syringe.

16 Claims, 11 Drawing Sheets

(52) U.S. Cl.
CPC .... *A61M 5/31551* (2013.01); *A61M 5/31591* (2013.01); *A61M 5/31553* (2013.01); *A61M 2005/5033* (2013.01)

(58) Field of Classification Search
CPC ...... A61M 5/31591; A61M 2005/5033; A61M 2205/273; A61M 5/31553
See application file for complete search history.

(56) References Cited

U.S. PATENT DOCUMENTS

| | | |
|---|---|---|
| 2007/0167921 A1 | 7/2007 | Burren et al. |
| 2009/0054846 A1 | 2/2009 | Moser et al. |
| 2010/0010454 A1 | 1/2010 | Marshall et al. |
| 2012/0203184 A1 | 8/2012 | Selz et al. |
| 2012/0316508 A1 | 12/2012 | Kirchhofer |
| 2015/0250950 A1 | 9/2015 | Moser et al. |
| 2016/0175528 A1 | 6/2016 | Marshall et al. |
| 2016/0367760 A1 | 12/2016 | Bainton et al. |

FOREIGN PATENT DOCUMENTS

| | | | | |
|---|---|---|---|---|
| WO | 9004423 A1 | 5/1990 | | |
| WO | 2011088894 A1 | 7/2011 | | |
| WO | 2012118687 A1 | 9/2012 | | |
| WO | WO-2015032785 A1 * | 3/2015 | ........ | A61M 5/31553 |
| WO | 2016033701 A1 | 3/2016 | | |

* cited by examiner

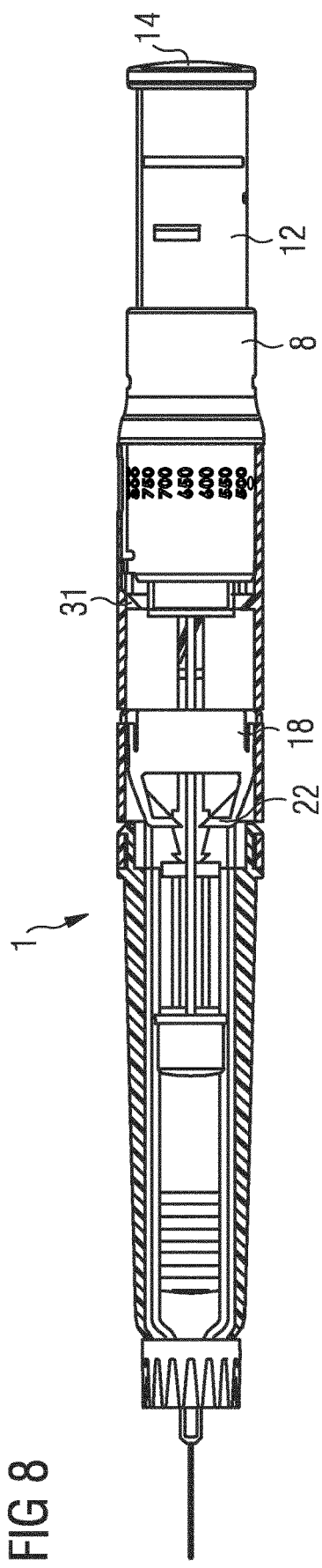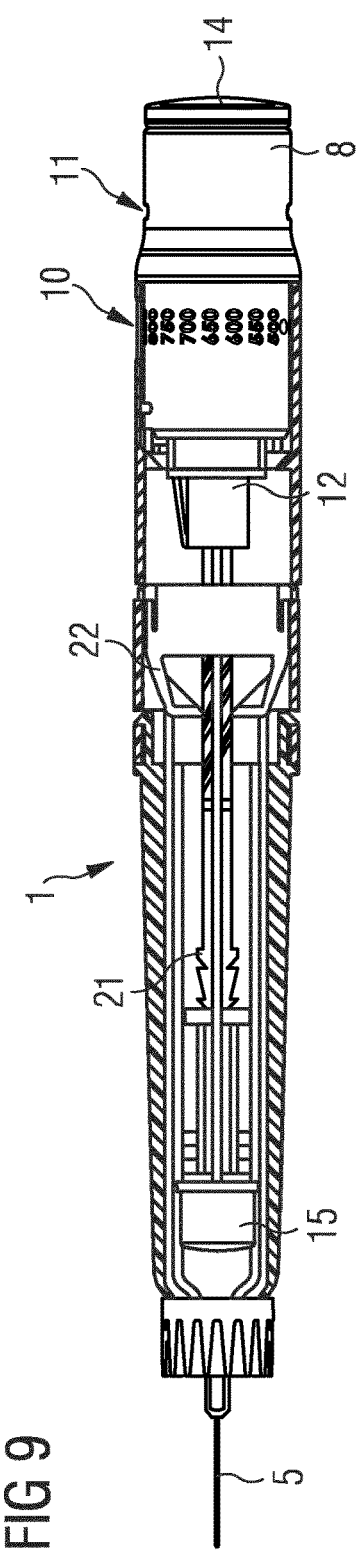

ASSEMBLY FOR A MEDICATION DELIVERY DEVICE AND MEDICATION DELIVERY DEVICE

CROSS REFERENCE TO RELATED APPLICATION

This application is a 371 of International Application No. PCT/EP2018/051877 filed Jan. 25, 2018, which claims the benefit of priority to European Patent Application No. 17154634.4 filed Feb. 3, 2017.

BACKGROUND OF THE INVENTION

Field of the Invention

The present disclosure relates to an assembly for a medication delivery device. The present disclosure further relates to a medication delivery device. The medication delivery device may be an injection device, such as an injection pen. The medication delivery device may be a variable-dose device. The medication delivery device may be a single-shot device.

In a variable-dose device the size of a dose to be dispensed is selectable by a user in a dose setting operation. In a single-shot device, only a single dose dispensing operation is enabled. After delivery of the single dose, the device may be locked such that a further dose delivery operation is prevented. Thereby, also a further dose dispensing operation is prevented.

SUMMARY OF THE INVENTION

It is an object of the present disclosure to provide an assembly for a medication delivery device having improved properties, increased user comfort, increased safety, reduced error-proneness and/or reduced manufacturing costs.

One aspect of the present disclosure relates to an assembly for a medication delivery device. The assembly comprises several mechanical components of the medication delivery device in their assembled state. In specific embodiments, the assembly may correspond to the entire medication delivery device.

The assembly comprises a body. The body may be designed to enable a safe and comfortable handling of the device. The body may be configured to house, fix, protect and guide inner components of the device. Preferably, the body limits or prevents the exposure of the inner components and/or the medication to contaminants such as liquid, dirt or dust. The body may be a unitary or multipart component.

As an example, the body may comprise a main part and a retainer part. The main part may be locked to the retainer part. The term "locking" describes an engagement where any relative movements between the engaged components are prevented. Alternatively, the main part and the retainer part may be a unitary component. The main part may house mechanical components of the assembly. The retainer part may retain the medicament. A cartridge containing the medicament may be inserted in the retainer part. Alternatively, the retainer part may directly retain the medicament without that an additional cartridge is provided.

The assembly comprises a dose setting part enabling selecting a size of a dose by a user. Operating the dose setting part may also include the preparation of the assembly for a subsequent dose dispensing operation. The dose setting part is configured to be directly operated, in particular gripped, by a user. The dose setting part may have the shape of a sleeve.

The assembly further comprises a piston rod configured to be moved axially without rotating for dispensing a medication. The piston rod may be permanently prevented from rotation. As an example, the piston rod may be splined to the body or to a component locked to the body. The piston rod may be an elongate component. The piston rod may be configured to act on a dose in the retainer part, wherein the dose is in direct contact with the medicament. Alternatively, the distal end of the piston rod may be in direct contact with the medicament.

A proximal movement of the piston rod, in particular during dose setting, may be prevented by a non-return member. The non-return member may be a component being permanently locked to the body, e.g., by a snap-fit connection. The non-return member may comprise one or more ratchet arms for engagement of one or more teeth of the piston rod. Each tooth may have a steep proximal side face preventing a proximal movement of the piston rod by the ratchet arm abutting the proximal side face. The tooth may have a less steep distal side face allowing the ratchet arm to snap over the tooth for enabling a distal movement of the piston rod. The non-return member may also prevent a rotation of the piston rod.

In general, the term "distal" or "distal end" refers to that end of the device or a component thereof that is closest to a dispensing end of the device. The term "proximal" or "proximal end" refers to that end of the device or a component thereof that is furthest away from the dispensing end of the device. The term "distal direction" or "distally" refers to the direction defined by a line from the proximal end to the distal end of the device or a component. The term "proximal direction" or "proximally" refers to the opposite direction, i.e., defined by a line from the distal end to the proximal end.

The assembly may comprise a longitudinal axis. The longitudinal axis may be defined by a linear connection of the distal and the proximal end. The longitudinal axis may be a symmetry axis of the assembly.

The assembly further comprises a drive member being directly coupled to the piston rod. The drive member is configured to drive the piston rod distally in a dose dispensing operation. The drive member may have the shape of a sleeve. The drive member may protrude out of the body during a dose setting operation. In particular, a least a part of the drive member may be visible for a user during dose setting. The drive member may be configured to rotate and move in an axial direction during dose setting.

The drive member may be in threaded engagement with the piston rod. The assembly may be configured such that a relative movement of the drive member and the piston rod during dose setting is enabled. A relative movement of the drive member and the piston rod during dose dispensing may be prevented.

The drive member may be configured to move in a proximal direction in a dose setting operation. In particular, the movement of the drive member in the proximal direction may result in the drive member protruding more and more out of the body. Thereby, the overall length of the device increases. This may help to increase the user safety of the device, because the extent of protrusion of the drive member indicates for a user that a particular dose is set.

The assembly may comprise a dose dispense part configured to be directly operated by a user for dispensing a dose. The dose dispense part may be a part of a button-like component. The dose dispense part may be an integral part of the drive member or may be a component permanently locked to the drive member. In these cases, the movement of the dose dispense part in a distal direction directly results in the same movement of the drive member. This increases user safety as the user has direct control over the drive member.

In an embodiment, the dose setting part is coupled to the drive member such that a relative movement of the dose setting part and the drive member is enabled. The dose setting part may be partially retained in the body. A relative movement of the dose setting part and the drive member may occur during a dose setting operation and/or a dose dispensing operation. The drive member may be at least partially retained in the dose setting part.

The dose setting part may be directly coupled to the drive member. The dose setting part may be in splined connection with the drive member. As an example, the dose setting part may comprise an axial groove engaged with a protrusion of the drive member or vice versa. The protrusion may be an elongate axial rib.

The dose setting part may be configured to be rotated for setting a dose, wherein a movement in axial direction is disabled. As an example, the body may comprise a circumferential protrusion engaged with a recess in the dose setting part. The circumferential protrusion may have an opening, i.e., may not extend over the whole circumference. The opening may be provided for enabling parts of the drive member to pass the protrusion when moving in a proximal direction during dose setting.

In an embodiment, the drive member comprises the dose setting part or the dose setting part is permanently locked to the drive member. As an example, the dose setting part may be a cap-shaped component fixed to the drive member, e.g., by a snap-fit connection. In this case, the dose setting part may be configured to be rotated and moved in an axial direction for setting a dose.

The drive member may be configured to, in a dose dispensing operation, axially move in the distal direction while being prevented from rotating. Such an axial movement may be prevented by an engagement part being guided in an axial track of the body or of a component permanently locked to the body, e.g., the non-return member. The track may be a groove.

The engagement part may be any part suitable to be received and guided in the track. For example, the engagement part may be a protrusion, in particular a rib. The body or the component locked to the body may comprise a plurality of such tracks.

The engagement part may be enabled to disengage, engage and/or override one or more of the tracks in a dose setting operation. In particular, the engagement part may be a rotational detent. When the engagement part engages and/or overrides a track, an audible and/or tactile feedback may be produced. This may indicate to a user that a discrete size of a dose has been reached. The tracks may be configured to ensure that only discrete doses can be set. In a dose dispensing operation, the engagement part is configured to be engaged in one of the tracks. This may facilitate the dose setting operation for the user and may improve dosing accuracy.

In an embodiment, the dose setting member comprises the engagement part. In this case, the dose setting member is directly coupled to the body or to a component locked to the body.

In an alternative embodiment, the drive member comprises the engagement part. In this case, the drive member is directly coupled to the body or to a component locked to the body.

According to an embodiment, the assembly is configured such that a dose setting operation is disabled until a priming operation has been carried out. The priming operation comprises advancing the drive member in a distal direction. Thereby, the drive member may advance the piston rod in the distal direction and a small priming dose may be dispensed from the device. By the movements of the components of the assembly, manufacturing tolerances may be removed and the dosing accuracy for a subsequent dose setting and dose dispensing operation may be ensured. Furthermore, priming may serve to remove air bubbles in the cartridge.

In the unprimed state of the device, a rotation of the dose setting part may be prevented. The dose dispense part may be enabled to be pushed in an unprimed state. A priming operation may be carried out by pushing the dose dispense part towards the body.

The drive member or a component permanently locked to the drive member may comprise a prime-lock part preventing a rotation of the dose setting part in the unprimed state. The prime-lock part may indirectly or directly cooperate with a further prime-lock part of the body or a component locked to the body. In the unprimed state, the prime-lock part and the further prime-lock part may be axially aligned.

In an embodiment, one of the above-described tracks in the body or in a component locked to the body functions as the further prime-lock part. The track may indirectly interact with the prime-lock part. In particular, the prime-lock part may block the engagement part of the dose setting part from disengaging the track. In an unprimed state, the prime-lock part may be located radially beneath the deflectable part where the engagement part is located, such that a radial inwards deflection of the engagement part is prevented. As an example, the prime-lock part may have the shape of a radially protruding wall.

In an embodiment, the body or a component locked to the body may comprise one or more further prime-lock parts directly interacting with the prime-lock part of the drive member. As an example, in the unprimed state, the further prime-lock parts may be located rotationally adjacent to the prime-lock part. The prime-lock part and the further prime-lock part may have the shape of short ribs. When a rotational force is applied to the dose setting part and when the rotational force is transmitted to the drive member, the prime-lock part abuts the further prime-lock part, thereby preventing a rotation of the drive member and the dose setting part. The prime-lock part may be located between two further prime-lock parts. In this case, a rotation in either direction can be prevented by the further prime-lock parts.

For carrying out a priming operation, the dose dispense part may be pushed in a distal direction. Thereby, also the drive member with the prime-lock part moves in a distal direction, e.g., without rotating. A rotation may be prevented by the engagement part being guided in one of the tracks. By the distal movement of the drive member, the prime-lock part may move towards an axial offset from the further prime-lock part. Due to this offset, a rotation of the dose setting part is now enabled.

In a dose setting operation, a direct or indirect interaction of the prime-lock parts may have to be prevented. In case that the drive member carries out a movement in a proximal direction during dose setting, the prime-lock part may have to pass the engagement part or the further prime-lock part.

In embodiments where the prime-lock part interacts with the deflectable part of the dose setting part, an inner surface of the body or a component locked to the body may be formed such that the deflectable part is not deflected radially inwards when the prime-lock part passes the deflectable part. In particular, the inner surface may have a radially outwards recessed area, at which the deflectable part is located when the prime lock part passes the deflectable part.

In embodiments where the prime-lock part directly interacts with one or more further prime-lock parts of the body, the prime-lock part of the drive member and the further prime-lock part of the body may be located at an angular offset when the prime-lock part passes the further prime-lock part. Due to the angular offset, an interaction of the prime-lock parts is prevented. The angular offset may be achieved by a rotational movement of the drive member in a dose setting operation.

The assembly may have a locked-out state, in which a further dose setting and/or dose dispensing operation is prevented. In particular, the locked-out state may be acquired once a single dose has been set and dispensed. In this case, the device is a single-use device.

The drive member may comprise a lock-out part. The body or a component permanently locked to the body may comprise a further lock-out part. The component may be the non-return member. In the locked-out state, the further lock-out part may block a movement of the lock-out part. In particular, a proximal movement of the lock-out part may be blocked.

The lock-out part may be deflectable radially inwards. The lock-out part may have the shape of an arm supported only at one end by a main part of the drive member. In particular, the lock-out part may be configured as a cantilever. The lock-out part may be enabled to pass the further lock-out part during a dose dispensing operation. In particular, the lock-out part may snap over the further lock-out part at the end of a dose dispensing operation. Thereby, an audible and/or tactile feedback may be produced, indicating the end of a dose dispensing operation to a user.

The further lock-out part may comprise a protrusion, in particular a protrusion protruding radially inwards. The protrusion may be a circumferential protrusion. The protrusion may be the same protrusion by which an axial movement of the dose setting part is prevented. The protrusion may have an opening, enabling the lock-out part to pass the protrusion when the drive member moves in a proximal direction during dose setting. In case that the drive member carries out a rotational movement during dose setting, the lock-out part is at an angular offset from the opening when the drive member moves in a distal direction during dose dispense. Thereby, an interaction of the lock-out part with the protrusion occurs during a dose dispensing operation, while an interaction is prevented during a dose setting operation.

According to a further aspect, a medication delivery device comprising the assembly is disclosed. The assembly may be integrated in the device, or may correspond to the entire device. The device may be an injection device. The device may by a pen-type device. The device may comprise or be used with a cartridge comprising a medication. Alternatively, the device may be used without a separate cartridge. The device may be a syringe, e.g., a syringe pre-filled by a medication.

The device may be supplied to the user in an unprimed state. Before setting a dose of a medication, the user may have to prime the device. The device may be a variable dose device such that the size of a dose to be dispensed can be chosen by a user. After delivery of a single dose of the medication, the device may be locked such that a further dose setting and dose delivery operation may be prevented.

In the following, a set of advantageous aspects is described. The aspects are numbered to facilitate referencing features of one aspect in other aspects. The aspects relate to a prime lock which ensures that a priming operation has to be performed before a dose setting operation and a dose delivery operation can be performed. Thereby, a high dose accuracy can be ensured.

This is of particular relevance for a variable dose device. One reason which makes dose accuracy of a variable dose device so significant is that it is much more difficult to be accurate compared to a device delivering the entire contents of medication. This is because the device must perform the metering function.

The set of following set aspects comprises subject matters which may comprise any structural and functional feature described above.

1. An assembly for a medication delivery device,
   the assembly comprising a body,
   a piston rod configured to be moved distally in a dose dispensing operation,
   a drive member being directly coupled to the piston rod for driving the piston rod in a dose dispensing operation,
   wherein the drive member or a component locked to the drive member comprises a prime-lock part and wherein the body or a component locked to the body comprises a further prime-lock part, wherein the prime-lock part and the further prime-lock part directly or indirectly interact with each other, thereby preventing a dose setting operation prior to a priming operation.

2. The assembly of aspect 1,
   wherein the drive member comprises an engagement part which in the unprimed state engages an axial track in the body or in a component locked to the body, wherein the prime-lock part blocks the engagement part from disengaging the track in the unprimed state.)

3. The assembly of aspect 2,
   wherein in the unprimed state the prime-lock part is located radially beneath the engagement part, thereby blocking a radial deflection of the engagement part.

4. The assembly of aspect 1,
   wherein the body or a component locked to the body comprises a further prime-lock part, wherein the prime-lock part and the further prime-lock part abut with each other when a rotational force is applied to the dose setting part.

5. The assembly of any of aspects 1 to 4,
   wherein the prime-lock part is moved in a distal direction during a priming operation and, thereby, in an axial offset from the further prime lock-part.

6. The assembly of any of aspects 1 to 5,
   wherein the drive member moves in a proximal direction in a dose setting operation, wherein the prime-lock part passes the further prime lock-part and/or the engagement part in the dose setting operation.

7. The assembly of aspect 6,
   wherein the prime-lock part is enabled to pass the further prime-lock part due to a rotational movement of the drive member during a dose setting operation.

8. The assembly of aspect 6,
   wherein the prime-lock part is enabled to pass the engagement part due to the engagement part being not in an inwardly deflected state after priming.

9. The assembly of any of the foregoing aspects,
   comprising a dose setting part comprising a recess, wherein the body comprises a circumferential protrusion, wherein the recess is engaged with the circumferential protrusion for preventing an axial movement of the dose setting part, wherein the circumferential protrusion comprises an opening, wherein the prime-lock part is enabled to pass the circumferential protrusion through the opening in a dose setting operation.
10. The assembly of aspect 9,
    wherein the drive member comprises a lock-out part interacting with the circumferential protrusion for preventing a further dose setting operation once a dose has been set and dispensed.
11. The assembly of aspect 10,
    wherein at the end of a dose dispensing operation, the lock-out part and the opening are located at an angular offset from each other.

In the following, a further set of advantageous aspects is described. The aspects are numbered to facilitate referencing features of one aspect in other aspects. The aspects relate to a multi-functional non-return member. In particular, the non-return member may have structural and functional features which could be also fulfilled by the body. Such a non-return member may facilitate the assembly and/or reduce the complexity of the device.

Features which are described herein above and below in conjunction with different aspects or embodiments, may also apply for other aspects and embodiments. Further aspects, features and advantages of the present invention will be apparent from the following description of preferred embodiments with reference to the accompanying drawings.

BRIEF DESCRIPTION OF THE DRAWINGS

FIG. 8 schematically shows a sectional side view of the medication delivery after a dose setting operation.

FIG. 9 schematically shows a sectional side view of the medication delivery after a dose dispensing operation.

DETAILED DESCRIPTION OF THE INVENTION

Figure 1:
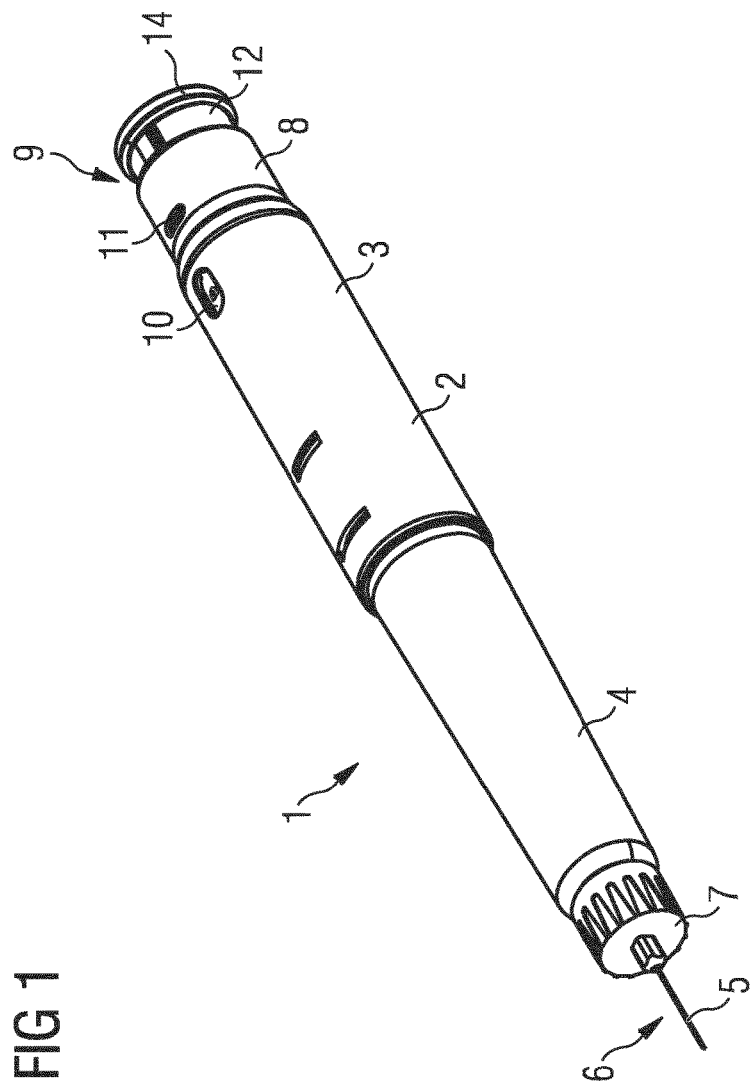
FIG. 1 schematically shows a perspective view of a medication delivery device.

Like elements, elements of the same kind and identically acting elements may be provided with the same reference numerals in the figures.

FIG. 1 shows a perspective view of a medication delivery device 1. The device 1 is adapted to retain a medication, in particular a liquid medication. The device 1 is a variable dose device such that the size of a dose to be administered is variable by a user.

The device 1 may be a single-shot device. This means that the device 1 is intended for a single use, i.e., for administering only one dose of medication. The device 1 may be configured to be primed before a dose is administered. The priming operation serves to remove tolerances between the mechanical components and does not comprise administering a dose of medication. After a single use, the device 1 may be discarded. The device 1 may comprise a lock-out mechanism which may prevent a further dose dispensing operation once a single dose has been dispensed. In particular, the lock-out mechanism may prevent a further dose dispensing operation by preventing a further dose setting operation.

The device 1 comprises a body 2. The body 2 may be designed to enable a safe and comfortable handling of the medication delivery device 1. The body 2 may be a unitary or multipart component. The body 2 may comprise a cylindrical shape. The device 1 may have a pen-type shape.

The body 2 comprises a main part 3 that may house, fix, protect and guide inner components of the device 1. The body 2 comprises a retainer part 4 for retaining the medication. The retainer part 4 may be a cartridge holder for holding a cartridge containing the medication. Alternatively, the medication may be directly retained in the body 2, in particular in the retainer part 4, without that a cartridge is provided. The retainer part 4 may be connected, e.g., snap-fitted or screwed to the main part 3. Alternatively, the retainer part 4 may be unitary with the main part 3.

The device 1 comprises a needle 5 at its distal end 6. The needle 5 may be part of a needle assembly 7 which may be connected, e.g., screwed to a distal end of the body 2, in particular to the distal end of the retainer part 4.

The device 1 comprises a dose setting part 8 for setting a dose of the medication. The dose setting part 8 is located near to the proximal end 9 of the device 1. The dose setting part 8 is configured to be directly operated by a user for setting a dose to be dispensed.

In particular, for setting a dose, the user grips the dose setting part 8 and rotates the dose setting part 8 until a desired size of the dose is selected. During such a dose setting operation, the dose setting part 8 may carry out a purely rotational movement. In an alternative embodiment, the dose setting part 8 may carry out a combined rotational and axial movement in the proximal direction.

The size of the set dose is visible through a window 10 provided in the body 2, in particular in the main part 3. The window 10 may also show specific states of the device 1. As an example, the window 10 may indicate that a dose setting operation has not been carried out yet. This state may be indicated by the numeral "P".

The device 1 may comprise a further window 11 for displaying specific states of the device 1. As an example, the further window 11 may indicate a primed state or a locked-out state of the device 1. The further window 11 may be located in the dose setting part 8, for example.

The device 1 further comprises a drive member 12 for driving a piston rod 13 (see FIG. 2) in a dose dispensing operation. The drive member 12 is directly coupled with the piston rod 13. In FIG. 1, the drive member 12 visibly protrudes out at of a proximal end of the body 2. This may indicate that the device 1 is ready to prime.

During a dose setting operation, the drive member 12 moves in a proximal direction whereby the overall length of the device 1 increases. The drive member 12 may carry out a combined rotational and axial movement during a dose setting operation.

The device 1 further comprises a dispense part 14 for dispensing a dose. The dispense part 14 is configured to be operated by a user, in particular pushed towards the body 2. The dispense part 14 is permanently locked to the drive member 12, for example by a snap-fit connection. The drive member 12 may carry out a purely axial movement in the distal direction during a dose dispensing operation. The dispense part 14 may have the shape of a cap.

The device 1 is shown in an unprimed state. A priming operation may be carried out by pushing the dispense part 14 towards the body 2.

Figure 2:
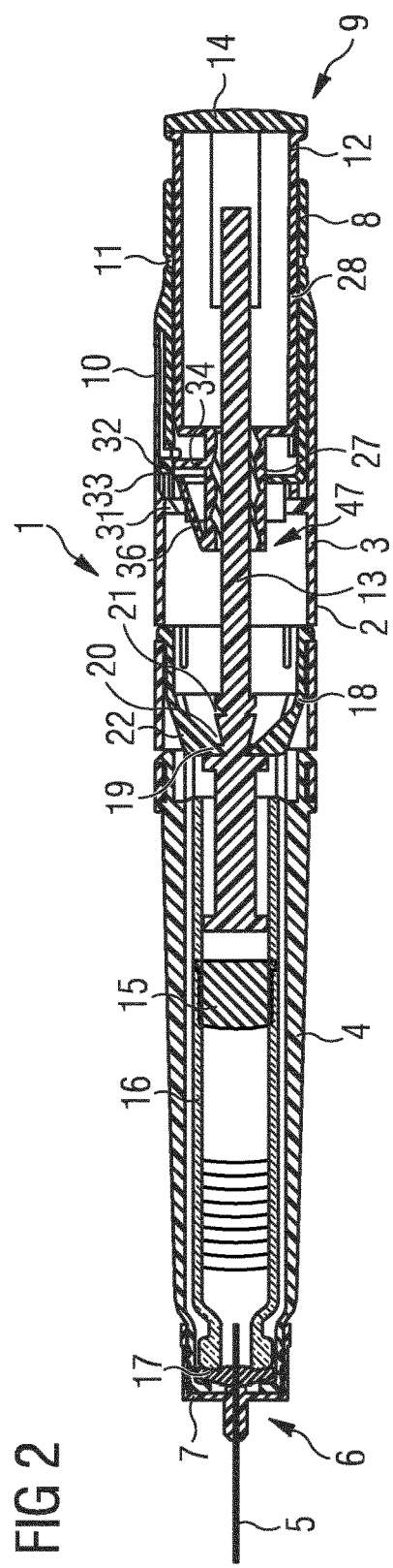
FIG. 2 schematically shows a cross-sectional view of the medication delivery device.
Figure 3:
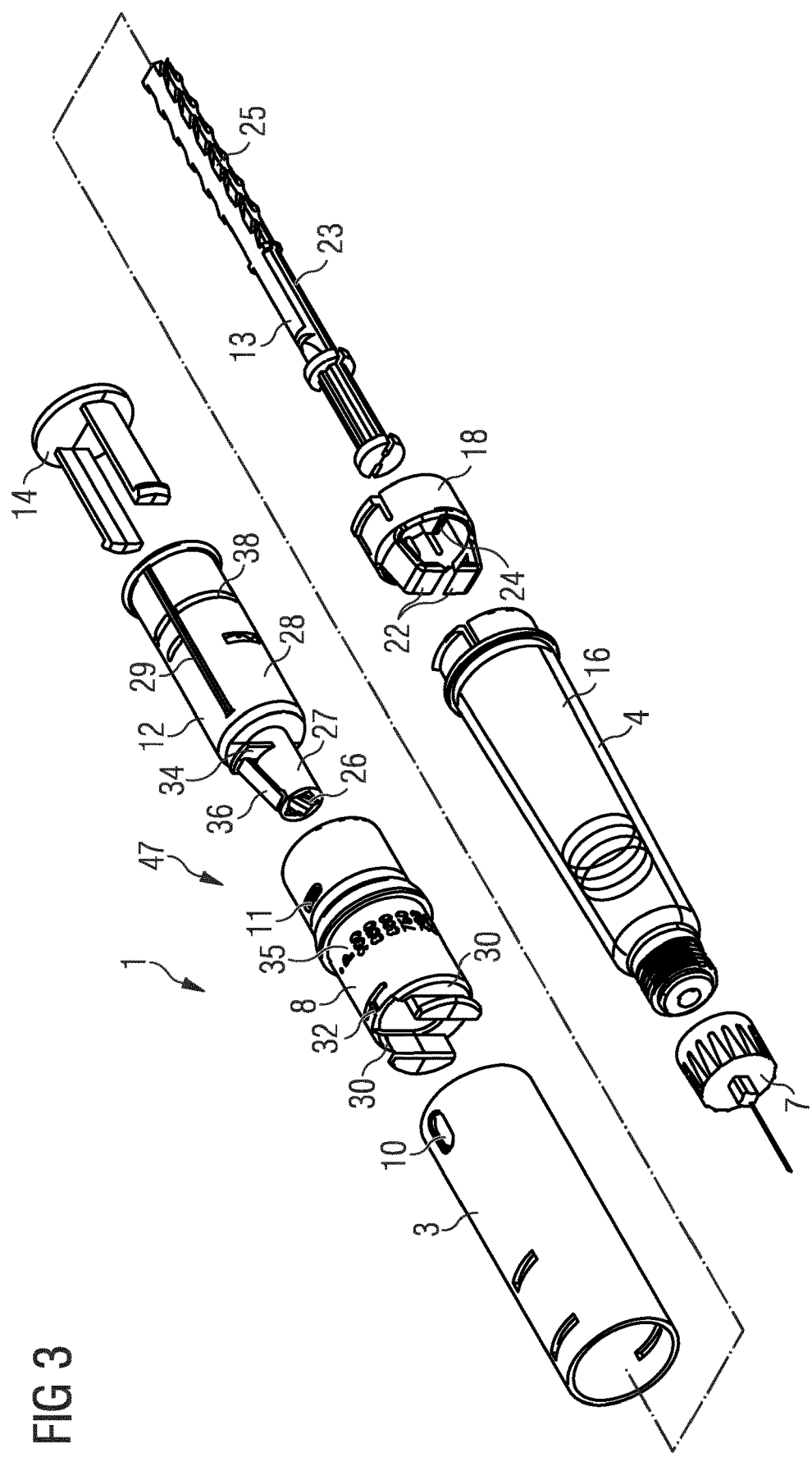
FIG. 3 schematically shows an exploded view of the medication delivery device.
Figure 4:
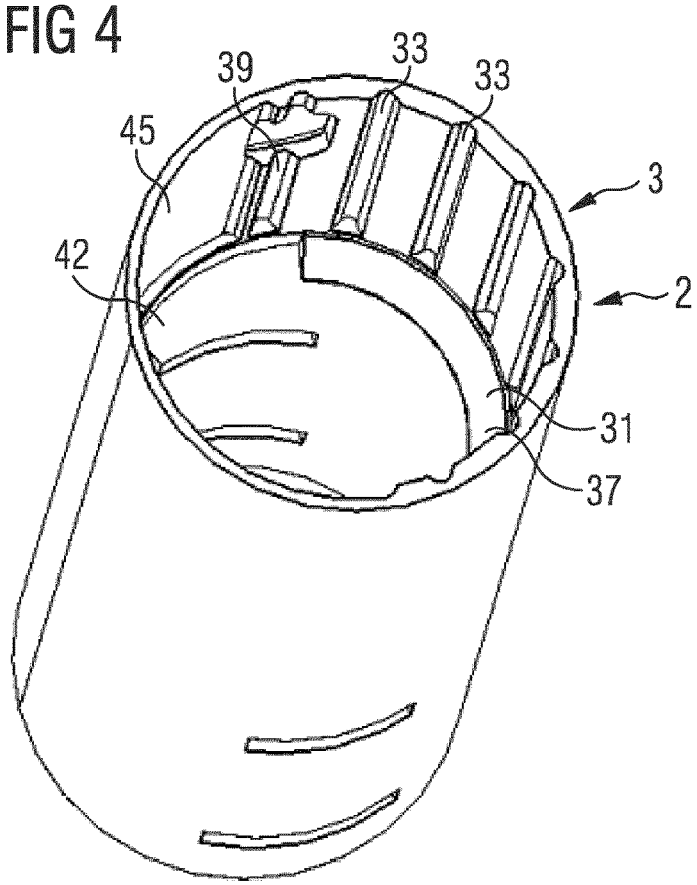
FIG. 4 schematically shows a perspective view of a main part of a body of the medication delivery device.
Figure 5:
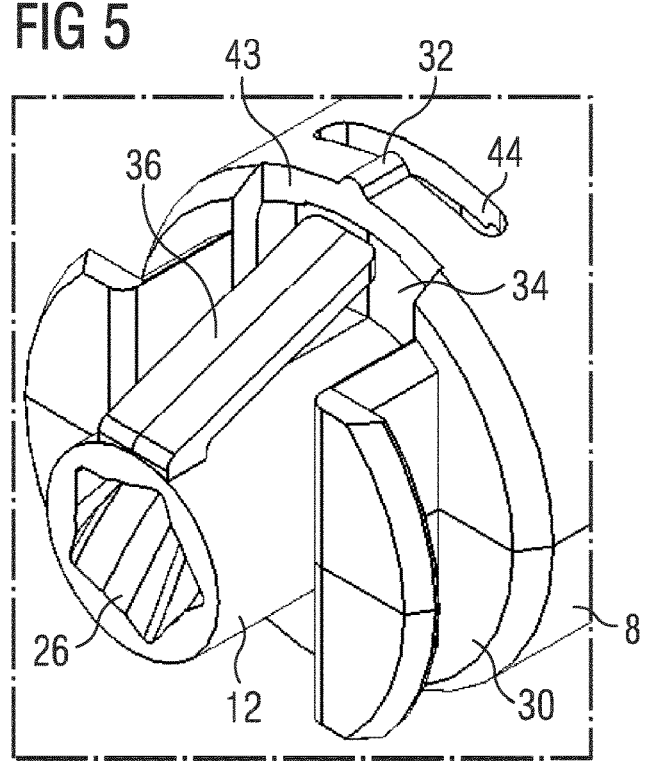
FIG. 5 schematically shows a perspective view of a detail of the drive member and the dose setting part during prime-lock.

In the following, the structure of the medication delivery device 1 is described in detail in connection with FIGS. 2, 3, 4 and 5, wherein FIG. 2 shows a cross-sectional view of the device 1, FIG. 3 shows an exploded view of the device 1, FIG. 4 shows a perspective view of the main part 3 of the body 2 and FIG. 5 shows a perspective view of a detail of the drive member 12 and the dose setting part 8 during prime-lock.

The piston rod 13 is an elongate component which is moved in the distal direction for expelling the medication. The piston rod 13 acts on a dose 15 retained in a cartridge 16. The cartridge 16 is sealed by a septum 17 pierced by the needle 5. In an alternative embodiment, the distal end of the piston rod 13 is in direct contact with the medicament and directly presses the medicament out of the device 1.

The piston rod 13 is axially movable in the distal direction with respect to the body 2 for expelling the medication. The piston rod 13 is permanently prevented from rotating relative to the body 2. A non-return member 18 is engaged with the piston rod 13 and prevents a movement of the piston rod 13 in the proximal direction. The non-return member 18 is permanently locked to the body 2. The non-return member 18 may be locked to the body 2 by a snap-fit connection, for example.

The piston rod 13 comprises several teeth 19, 20, 21 for engaging a ratchet arm 22 of the non-return member 18. A further ratchet arm 22 and corresponding teeth 19, 20, 21 are also provided on an opposite side of the piston rod 13 and the non-return member 18, respectively.

When the ratchet arm 22 is located at a proximal side of one of the teeth 19, 20, 21, a movement of the piston rod 13 in the proximal direction is prevented due to a steep proximal wall of each of the teeth 19, 20, 21. A movement in a distal direction is enabled by a less steep distal wall of each of the teeth 19, 20, 21. The force required for snapping over the teeth 19, 20, 21 is defined by the steepness of the distal walls.

The ratchet arm 22 snaps over the first and second tooth 19, 20 during a priming operation. The ratchet arm 22 snaps over the third tooth 21 during a dose setting operation. The distal walls of the first and third teeth 19, 21 are steeper than the distal wall of the second tooth 20 such that the user has to overcome an initial high resistance to start a priming and a dispensing operation, respectively.

The non-return member 18 also prevents a rotational movement of the piston rod 13. For this aim, the piston rod 13 comprises a groove 23 (see FIG. 3), extending in an axial direction. The groove 23 may extend along the full length of the piston rod 13. The non-return member 18 comprises an axial protrusion 24 (see FIG. 3) which is engaged with the groove 23 and, thereby, guides the piston rod 13 and prevents a rotational movement of the piston rod 13. Such a groove 23 and a corresponding protrusion 24 are provided at two opposite sides of the piston rod 13 and the non-return member 18, respectively.

In addition to that, a rotation of the piston rod 13 may additionally be prevented by the non-circular cross section of the piston rod 13 and the abutment of the ratchet arms 22 of the non-return member 18 on the piston rod 13. Alternatively or additionally, a part different from the non-return member 18 may prevent a rotational movement of the piston rod 13.

The piston rod 13 comprises a thread 25 (see FIG. 3) engaging a corresponding thread 26 (see FIG. 3) of the drive member 12. The threads 25, 26 may be configured as multi-start threads to increase the engagement strength of the threads 25, 26.

The drive member 12 has the shape of a sleeve and partially encloses the piston rod 13. The thread 26 of the drive member 12 is located at a distal part 27 (see FIG. 3) of the drive member 12. The distal part 27 has a smaller diameter than a proximal part 28 (see FIG. 3) of the drive member 12. The differing diameters are provided for allowing the drive member 12 to be engaged both with the piston rod 13 and with the dose setting part 8.

The drive member 12 is in splined engagement with the dose setting part 8. In particular, the drive member 12 comprises an elongate rib 29 (see FIG. 3) located at the proximal part 28 which engages an elongate groove (not depicted) in the interior of the dose setting part 8. A further elongate rib and a further elongate groove is located at an opposite side of the drive member 12 and the dose setting part 8, respectively. The splined engagement permanently prevents a rotational movement of the dose setting part 8 relative to the drive member 12.

The dose setting part 8 is axially fixed to the body 2 but rotatable relative to the body 2 for allowing a dose setting operation. In particular, the dose setting part 8 comprises one or more recesses 30 (see FIG. 3), which are engaged with a circumferential protrusion 31 (see FIG. 4) in the interior of the main part 3 of the body 2. The circumferential protrusion 31 has an opening 42 (see FIG. 4) which enables parts of the drive member 12 to pass the protrusion 31 and thereby, enable the drive member 12 to move proximally in a dose setting operation.

The dose setting part 8 comprises an engagement part 32 which is located at a deflectable part 43 of the dose setting part 8 (see FIG. 5). The deflectable part 43 may have the shape of a bridge being connected at both ends to a main part of the dose setting part 8. The deflectable part 43 may be defined by an opening 44 in the dose setting part 8. The deflectable part 43 is enabled to deflect radially inwards.

The engagement part 32 is configured to be engaged with a track 33 (see FIG. 4) in the main part 3 of the body 2 before priming, during priming and during a dose dispensing operation. The main part 3 of the body 2 comprises a plurality of such tracks 33 for allowing the setting and dispensing of doses in discrete steps. Each of the tracks 33 is an axially extending groove in an interior part of the body 2. In the unprimed state the engagement part 32 is engaged with a priming track 39.

The drive member 12 comprises a prime-lock part 34 which is located beneath the engagement part 32 in the unprimed state of the device 1. The prime-lock part 34 disables the deflectable part 43 and, thereby, the engagement part 32 from deflecting radially inwards and, thereby, disables the engagement part 32 from disengaging the track 33, in particular the priming track 39. Thereby, in the unprimed state, a rotation of the dose setting part 8 is prevented. Accordingly, the prime-lock part 34 blocks the device 1 from being used in a dose setting operation and a dose dispensing operation until a priming operation has been carried out.

The dose setting part 8 carries markings 35 on its outer surface visible through the window 10 in the main part 3. The markings 35 indicate the size of a set dose. The markings 35 may comprise dose numbers. Furthermore, the marking 35 may comprise one or more symbols indicating a specific state of the device 1.

The drive member 12 comprises a lock-out part 36 for locking the device 1 after a dose dispensing operation. The lock-out part 36 comprises a deflectable protrusion. The protrusion may have the shape of a cantilever. At the end of a dispensing operation, the lock-out part 36 may snap over the circumferential protrusion 31. The circumferential protrusion 31 has a steep distal side face such that a backwards movement of the lock-out part 36 is prevented. The circumferential protrusion 31 has a less steep proximal side face such that the lock-out part 36 is enabled to snap over the circumferential protrusion 31 when being moved in a distal direction. The circumferential protrusion 31 is a further lock-out part 37, interacting with the lock-out part 36.

The drive member 12 carries one or more markings 38 on its outer surface for indicating specific states of the device 1. In particular, the markings 38 comprise one or more colored rings. The markings 38 may indicate a pre-primed state or a locked state of the device 1, for example. The markings 38 are visible through the further window 11 at certain states of the device 1.

The assembled mechanical components such as the drive member 12, the piston rod 13 and further components may be denoted as an assembly 47 of the device 1.

In the following, the operation of the medication delivery device 1 is described in detail in connection with FIGS. 6, 7, 8 and 9. The figures show the body 2 in a cross-sectional view and the further components of the medication delivery device 1 in a perspective view.

Figure 6:
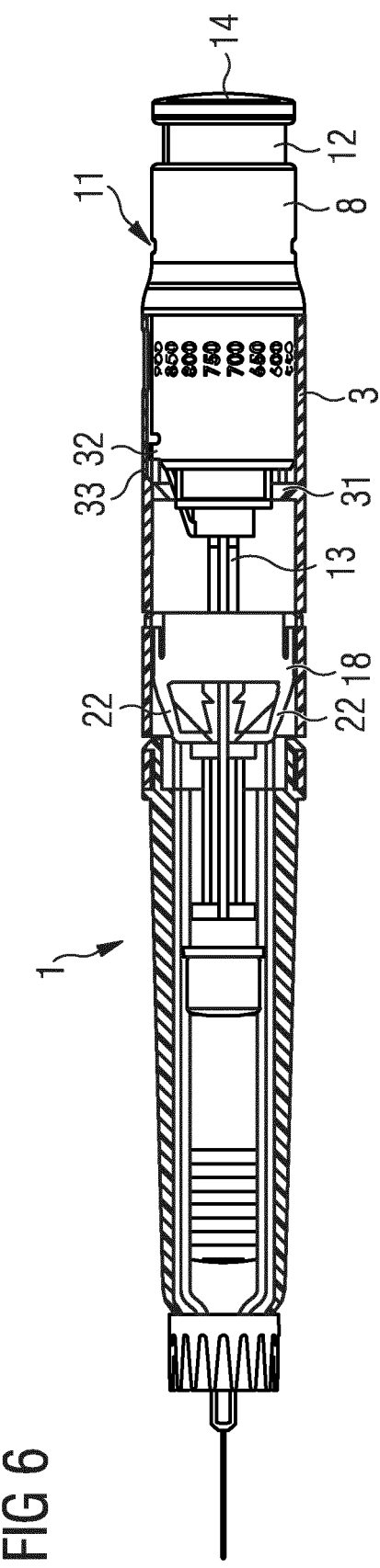
FIG. 6 schematically shows a sectional side view of the medication delivery as supplied from the manufacturer.

FIG. 6 shows the device 1 as supplied from the manufacturer. The device 1 is in an unprimed state.

The unprimed state may be indicated by a specific color visible in the further window 11. In particular, one of the markings 38 embodied as colored rings located on the drive member 12 is visible. The priming operation serves to remove the tolerances between mechanical components. In the priming operation, a small amount of medication may be pressed out of the device 1 without being administered to a user.

In the unprimed state, a dose setting operation is prevented by the prime-lock part 34 (see FIG. 5) of the drive member 12 holding the engagement part 32 of the dose setting part 8 in engagement with the track 33 in the body 2. The track 33 functions as a further prime-lock part 41, interacting indirectly with the prime-lock part 34 via the engagement part 32. In particular, the further prime-lock part 41 may correspond to a priming track 39 adjacent to a radially outwards recessed area 45 of the body 2. By the indirect interaction of the prime-lock parts 34, 41, a rotation of the dose setting part 8 relative to the body 2 is prevented. In this state, the drive member 12 protrudes out of the dose setting part 8.

For priming the device 1, the user pushes the dispense part 14 towards the body 2. Thereby, the drive member 12 is driven in the distal direction. A rotation of the drive member 12 is prevented by the splined engagement with the dose setting part 8 and by the engagement of the engagement part 32 of the dose setting member 8 in the axial track 33 in the body 2.

Due to the threaded engagement of the piston rod 13 with the drive member 12, the piston rod 13 is driven in the distal direction by the distal movement of the drive member 12. The dose 15 is moved forward by the piston rod 13 and a priming dose is dispensed from the device 1.

During the advancement of the piston rod 13, each ratchet arm 22 moves over the first priming tooth 19 and over the second priming tooth 20. The snapping of the ratchet arms 22 over the second priming teeth 20 indicates the end of the priming operation by an audible and tactile feedback.

Figure 7:
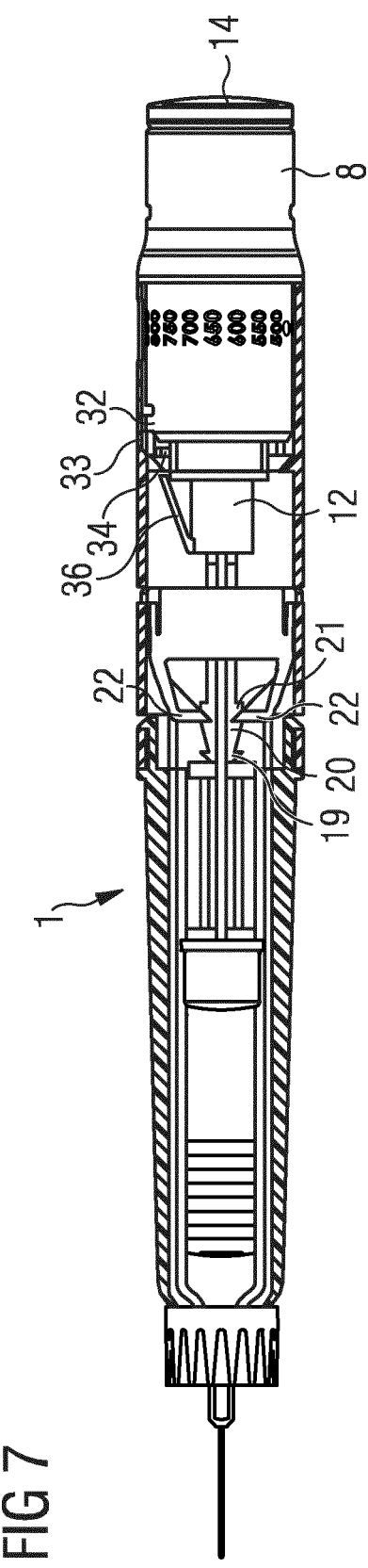
FIG. 7 schematically shows a sectional side view of the medication delivery in a primed state.

FIG. 7 shows the device 1 in its primed state, i.e., after a priming operation has been performed.

The dispense part 14 is fully depressed. The primed state of the device 1 is indicated by a different color appearing in the further window 11.

Each ratchet arm 22 is located between the second priming tooth 20 and the third tooth 21.

The prime-lock part 34 of the drive member 12 is located at a distal offset from the engagement part 32. The engagement part 32 is now free to deflect radially inwards and disengage from the track 33 when a rotational force is applied to the dose setting part 8.

In this state, a rotation of the dose setting part 8 and, thereby, a setting of a dose is enabled.

FIG. 8 shows the device 1 after a dose setting operation.

For setting a dose, the user grips and rotates the dose setting part 8, e.g., in an anti-clockwise direction when viewing from the proximal end towards the distal end. A rotation of the dose setting part 8 in the opposite direction may be prevented due to the specific shape of the sidewalls of the tracks 33 in the main part 3 of the body 2. In an alternative design, a rotation in the opposite direction may be allowed, e.g., to reduce the set dose.

During the rotation of the dose setting part 8, the engagement part 32 moves over the tracks 33 until a desired dose is set and displayed in the window 10. Each time the engagement part 32 engages with one of the tracks 33 an audible and/or tactile feedback may be produced. Accordingly, during dose setting, the increase of the size of the dose is indicated in a step-like manner. When the desired dose has been set, the engagement part 32 is engaged in one of the tracks 33 and the device is ready for a dispensing operation.

During the dose setting operation, the dose setting part 8, carries out a purely rotational movement due to the coupling with the body 2. Due to the splined engagement of the dose setting part 8 with the drive member 12, the drive member 12 is rotated. In addition to that, due to the threaded coupling of the drive member 12 with the piston rod 13, the drive member 12 also moves in a proximal direction. A proximal movement of the piston rod 13 is prevented by the ratchet arms 22 of the non-return member 18.

The circumferential protrusion 31 has an opening 42, which enables the lock-out part 36 of the drive member 12 to pass the circumferential protrusion 31. Furthermore, at the start of a dose setting operation, the engagement part 32 first moves along an area 45 recessed radially outwards, which enables the lock-out part 36 to pass the engagement part 32.

During the dose setting operation, the overall length of the device 1 increases. Now, the device 1 is ready for delivering the set dose of the medication.

FIG. 9 shows the device 1 after the dose has been dispensed.

For delivering the set dose, the user fully depresses the dispense part 14. Thereby, the drive member 12 is moved in a distal direction. A rotation of the drive member 12 is prevented by the splined engagement of the drive member 12 with the dose setting part 8 and by the engagement of the engagement part 32 of the dose setting part 8 in a track 33 in the body 2. Accordingly, the dose setting part 8 does not move during a dose dispensing operation. The dose displayed in the window 10 does not change during the dose dispensing operation.

Due to the threaded engagement of the drive member 12 with the piston rod 13, the piston rod 13 is driven in the distal direction. The third tooth 21 passes the ratchet arm 22 and the ratchet arm 22 slides along a flat surface of the piston rod 13. The piston rod 13 pushes the dose 15 further in distal direction, thereby expelling medication through the needle 5.

Due to the rotation of the drive member 12 in the dose setting operation, the drive member 12 is in a different rotational orientation than at the beginning of the dose setting operation. In particular, the lock-out part 36 is located at an angular offset from the opening 42 and is not aligned with the opening 42. In this orientation, the lock-out part 36 interacts with the circumferential protrusion 31 at the end of the distal movement of the drive member 12. In particular, the lock-out part 36 deflects and snaps over the circumferential protrusion 31. A backwards movement of the lock-out part 36 is prevented by a steep distal face of the circumferential protrusion 31. Thereby, a proximal movement of the drive member 12 is disabled and a setting of a further dose of medication is prevented. Accordingly, the circumferential protrusion 31 is a further lock-out part.

The device 1 is now locked. No further dose of the medication can be set and dispensed from the device 1. The locked state is indicated by a specific color appearing in the further window 11.

FIGS. 10 to 17 relate to a second embodiment of a medication delivery device 1. In the following, primarily the main differences to the first embodiment shown in the foregoing figures are described in detail. The further structural and functional elements may correspond to the first embodiment.

Figure 10:
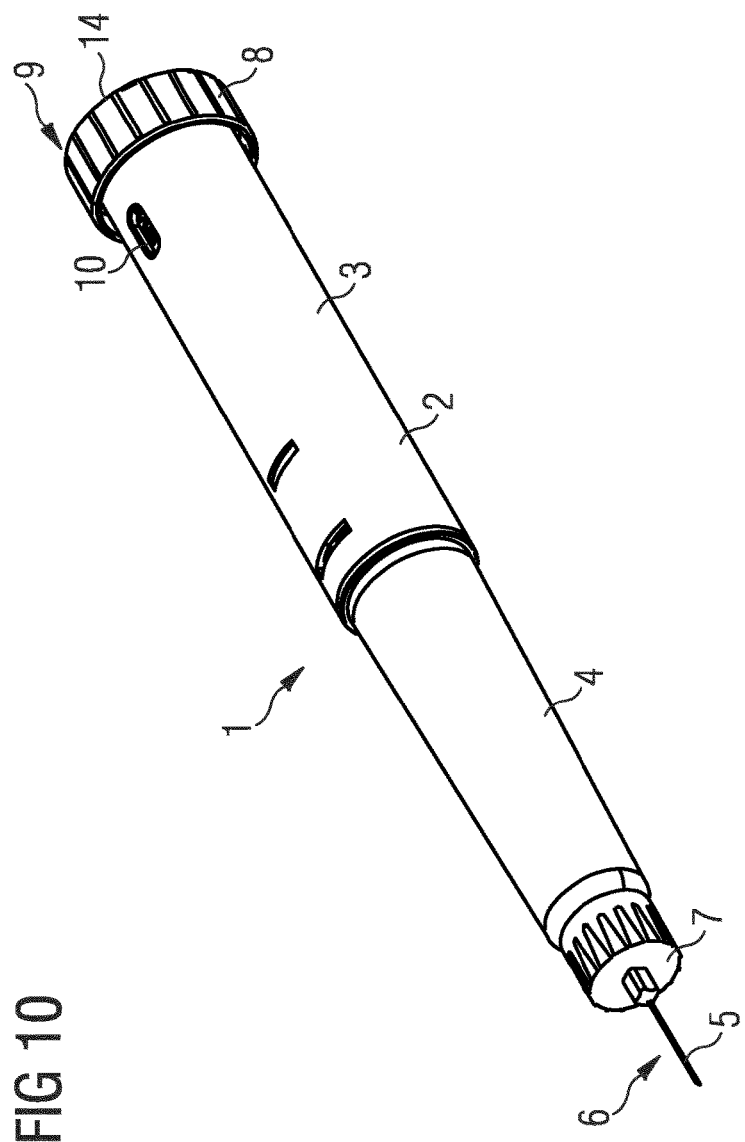
FIG. 10 schematically shows a perspective view of a medication delivery device according to a second embodiment.

FIG. 10 shows a perspective view of the second embodiment of a medication delivery device 1.

The device 1 comprises a dose setting part 8 for setting and, thereby selecting a size of a dose. The dose setting part 8 is unitary or permanently locked with the dispense part 14. The dose setting part 8 and the dispense part 14 are permanently locked with the drive member 12 (see FIG. 11). Accordingly, the dose setting part 8 is not located at a component which carries out relative movements to the drive member 12.

The dose setting part 8 may be permanently locked to the drive member 12. The dose setting part 8 is snap-fitted to the drive member 12, for example. The dose setting part 8 is designed as a cap having a gripping surface at its side face.

In the second embodiment, the functions which the dose setting part 8 fulfills in the first embodiment are fulfilled in parts by the drive member 12 and in parts by the dose setting part 8 locked to the drive member 12. Accordingly, the second embodiment comprises one separately movable component less than the first embodiment.

The device 1 comprises only a single window 10. The window 10 displays the size of a selected dose and may additionally display specific states of the device 1.

Figure 11:
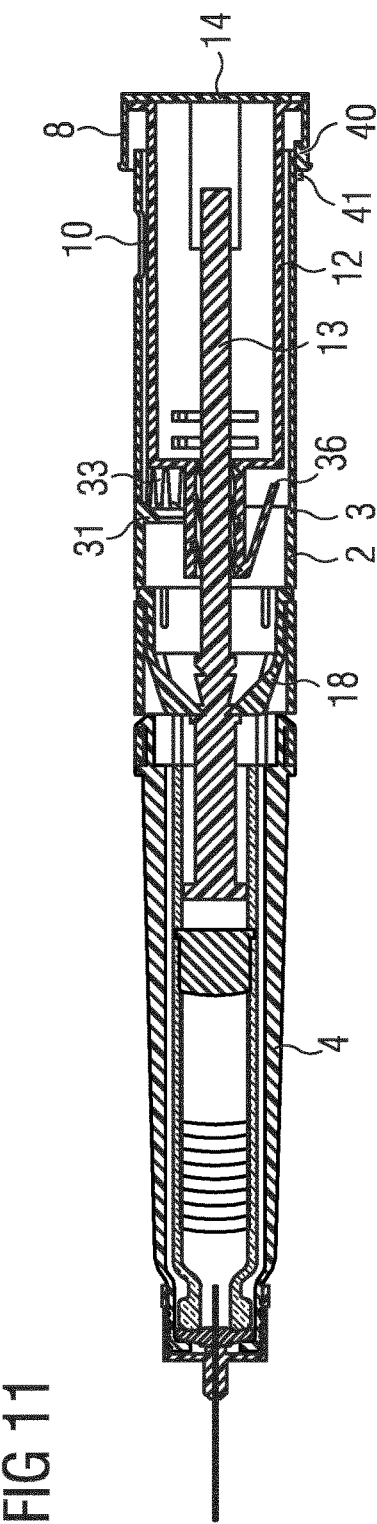
FIG. 11 schematically shows a cross-sectional view of the medication delivery device of the second embodiment.
Figure 12:
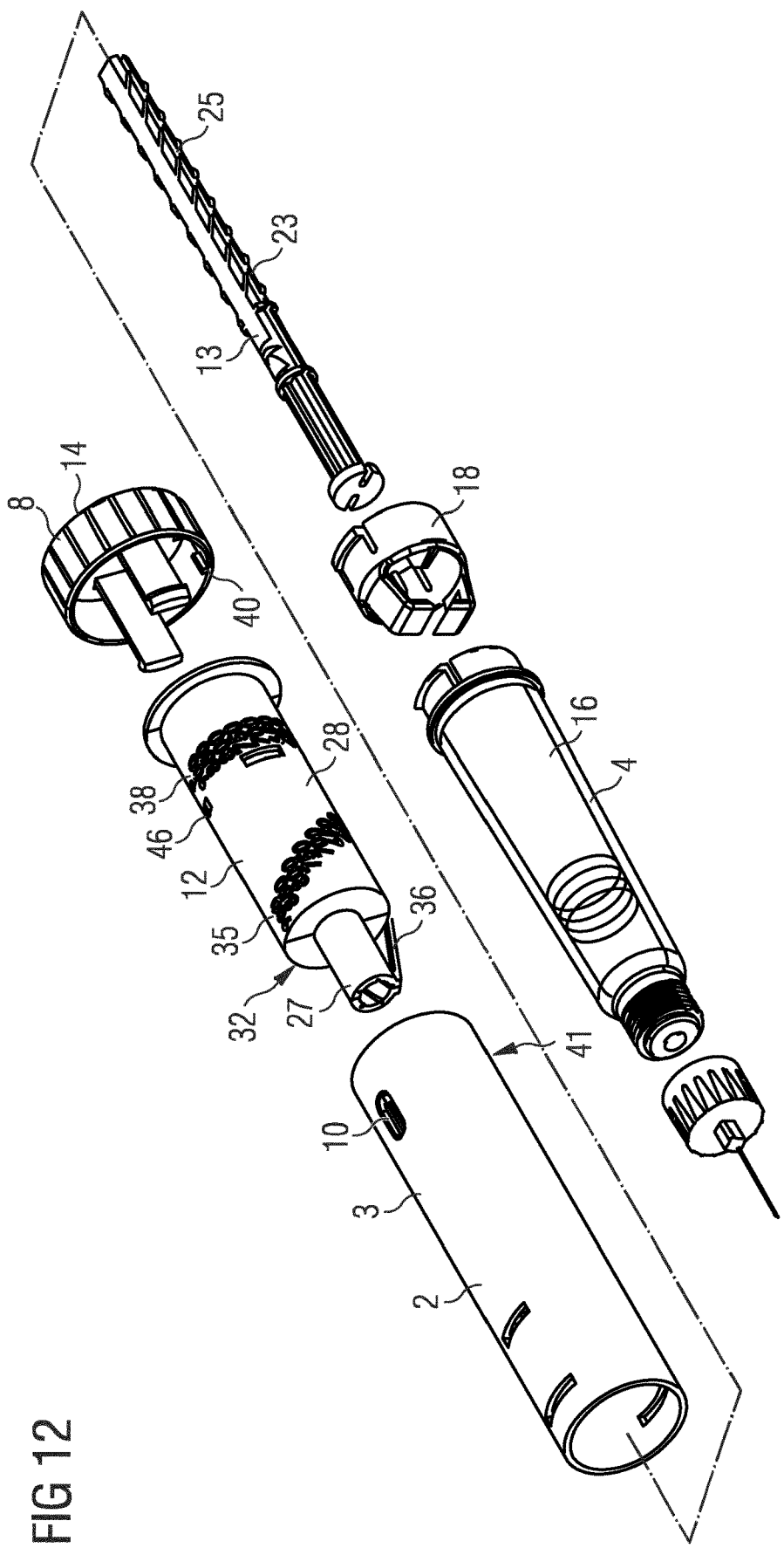
FIG. 12 schematically shows an exploded view of the medication delivery device of the second embodiment.
Figure 13:
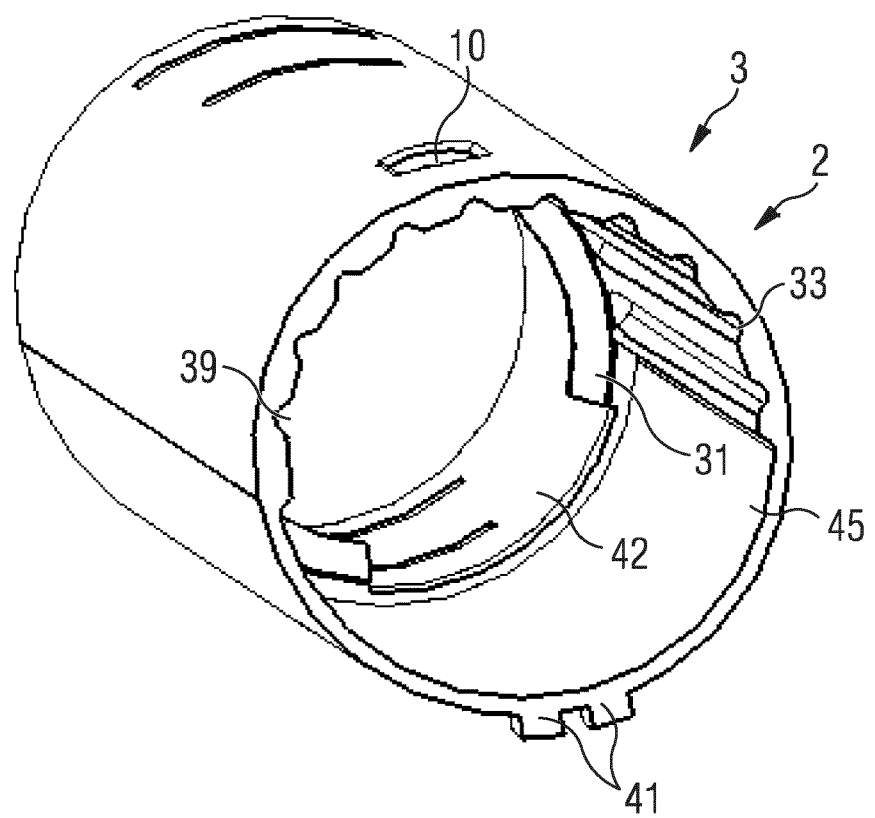
FIG. 13 schematically shows a perspective view of a main part of a body of the medication delivery device.

In the following, the structure of the medication delivery device 1 of the second embodiment is described in detail in connection with FIGS. 11, 12 and 13, wherein FIG. 11 shows a cross-sectional view of the medication delivery device 1, FIG. 12 shows an exploded view of the medication delivery device 1 and FIG. 13 schematically shows a perspective view of a main part 3 of the body 2 of the device 1.

The drive member 12 comprises an engagement part 32 corresponding to the engagement part 32 located on the dose setting part 8 of the first embodiment. The engagement part is not visible in FIG. 12, because it is located at an averted side of the drive member 12. The position of the engagement part 32 is indicated in FIG. 12.

The engagement part 32 is located at an inwardly deflectable part of the drive member 12. The deflectable part may have a bridge-like shape as described for the first embodiment. The engagement part 32 is configured to releasably engage axial tracks 33 (see FIG. 13) in the interior of the body 2.

The drive member 12 comprises several sets of markings 35, 38 and one prime-lock marking 46. The first set of markings 35 extends helically around the drive member 12. The second set of markings 38 extends circularly around the drive member 12. The different sets of markings 35, 38 are required in order to display the set dose both during setting and after a dispensing operation. Due to the axial movement of the drive member 12 in a dispensing operation, the first set of markings 35 is not visible through the window 10 after the dose is dispensed.

The dose setting part 8 comprises a prime-lock part 40 located at an inner surface. The prime-lock part 40 is a short rib extending in an axial direction. The prime-lock part 40 interacts with two further prime-lock parts 41 (see FIG. 13) located at an outer surface of the body 2. The further prime-lock parts 41 are located at the proximal end of the main part 3. The further prime-lock parts 41 are short ribs extending in the axial direction, arranged parallel to each other.

In an unprimed state of the device 1, the prime-lock part 40 is located between the further prime-lock parts 41. Thereby, any rotation of the dose setting part 8 is prevented.

In the following, the operation of the medication delivery device 1 is described in detail in connection with FIGS. 14, 15, 16 and 17. The figures show the body 2 in a cross-sectional view and the further components of the medication delivery device 1 in a perspective view.

Figure 14:
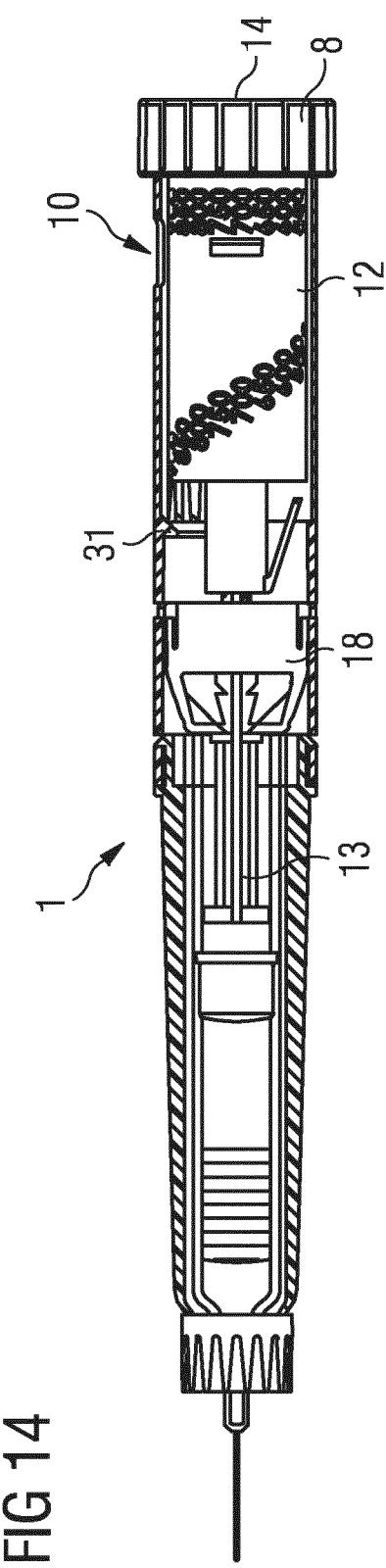
FIG. 14 schematically shows a sectional side view of the medication delivery of the second embodiment as supplied from the manufacturer.

FIG. 14 shows the device 1 as supplied from the manufacturer. The device 1 is in an unprimed state.

The unprimed state may be indicated by the prime-lock marking 46 (see FIG. 12) visible in the window 10. The prime-lock marking 46 may comprise a specific symbol, such as a symbol of a lock, or a color. Thereby, a user is informed that a priming operation is required before the device 1 is usable in a dose setting and dose dispensing operation.

In the unprimed state, a dose setting operation is prevented by the prime-lock part 40 of the dose setting part 8 being positioned between the prime-lock parts 41 at the body 2.

For priming the device 1, the user pushes the dispense part 14 and, thereby the drive member 12, towards the body 2. A rotation of the drive member 12 is prevented by the engagement of the engagement part 32 in one of the axial tracks 33 in the body 2.

Due to the threaded engagement of the piston rod 13 with the drive member 12, the piston rod 13 is driven in the distal direction and a small amount of medication is dispensed. The interaction of the non-return member 18 and the piston rod 13 is the same as described for the first embodiment.

Figure 15:
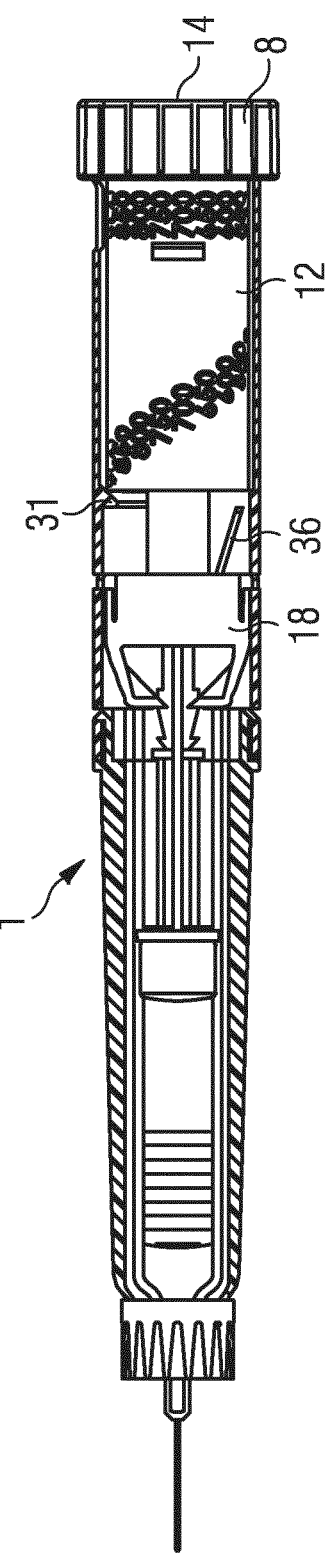
FIG. 15 schematically shows a sectional side view of the medication delivery of the second embodiment in a primed state.

FIG. 15 shows the device 1 in its primed state, i.e., after a priming operation has been performed.

The dispense part 14 is fully depressed. The primed state of the device 1 is indicated by a different color or symbol appearing in the window 10. In particular, one of the markings of the second set of markings 38 appears in the window 10. As an example a "P" may be displayed for indicating the primed state.

During the priming operation, the prime-lock part 40 on the dose setting part 8 moves out of engagement with the further prime-lock parts 41 of the body 2. The prime-lock part 40 are now located at an axial offset from the further prime-lock parts 41.

In this state, a rotation of the dose setting part 8 and, thereby, a setting of a dose is enabled.

Figure 16:
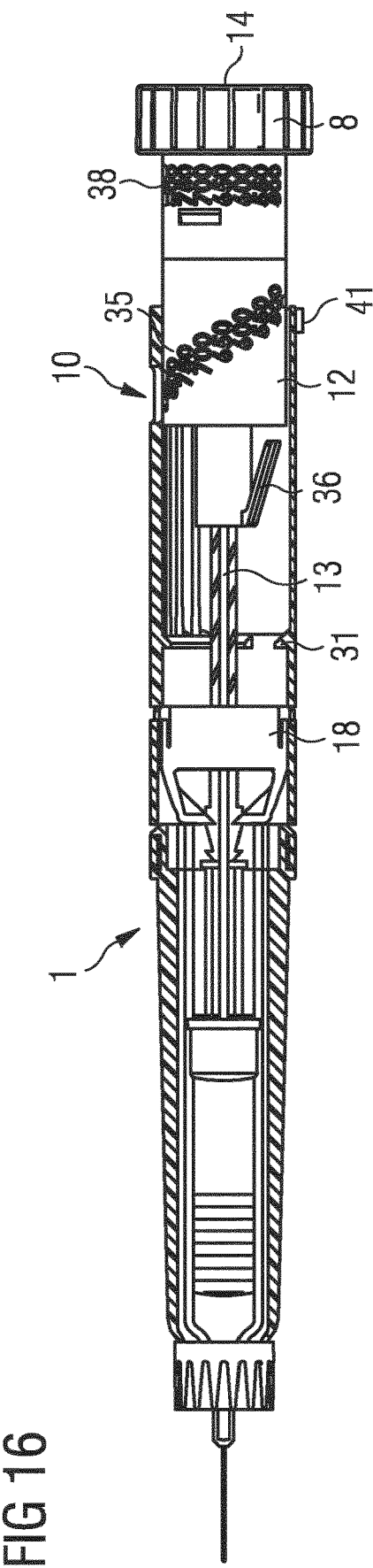
FIG. 16 schematically shows a sectional side view of the medication delivery of the second embodiment after a dose setting operation.

FIG. 16 shows the device 1 after a dose setting operation.

For setting a dose, the user grips and rotates the dose setting part 8. Due to the threaded engagement of the drive member 12 with the piston rod 13, the drive member 12, together with the dose setting part 8, moves in a proximal direction.

Due to the rotational movement of the dose setting part 8, the prime-lock part 40 is angularly misaligned from the further prime-lock parts 41 and, thereby, is enabled to ass the further prime-lock parts 41 when the dose setting part 8 moves in the proximal direction.

During the rotation of the dose setting part 8, the engagement part 32 moves over the tracks 33 until a desired dose is set and displayed by one of the markings of the first set of markings 35 appearing in the window 10. When the desired dose has been set, the engagement part 32 is engaged in one of the tracks 33 and the device 1 is ready for a dispensing operation.

During the dose setting operation, the overall length of the device 1 increases. Now, the device 1 is ready for delivering the set dose of the medication.

Figure 17:
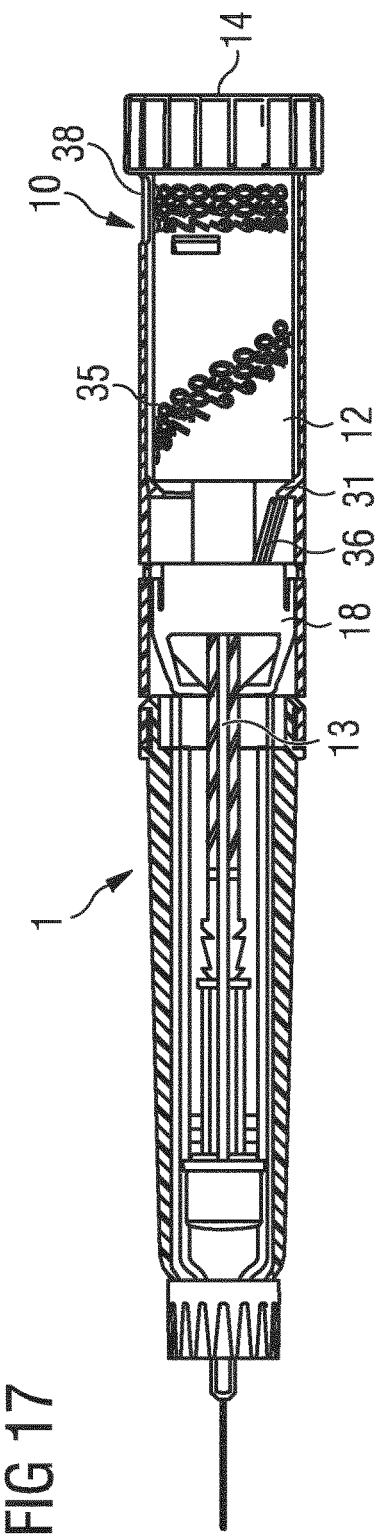
FIG. 17 schematically shows a sectional side view of the medication delivery of the second embodiment after a dose dispensing operation.

FIG. 17 shows the device 1 after the dose has been dispensed. For delivering the set dose, the user fully depresses the dispense part 14.

Thereby, the drive member 12 drives the piston rod 13 in a distal direction. A rotation of the drive member 12 is prevented by engagement of the engagement part 32 in a track 33 in the body 2.

The lock-out part 36 interacts with the circumferential protrusion 31 at the end of the dose dispensing operation, as described for the first embodiment, and locks the device 1. The locked state and/or the size of the dispensed dose is indicated by a specific marking of the second set of markings 38 appearing in the window 10.

Figure 18:
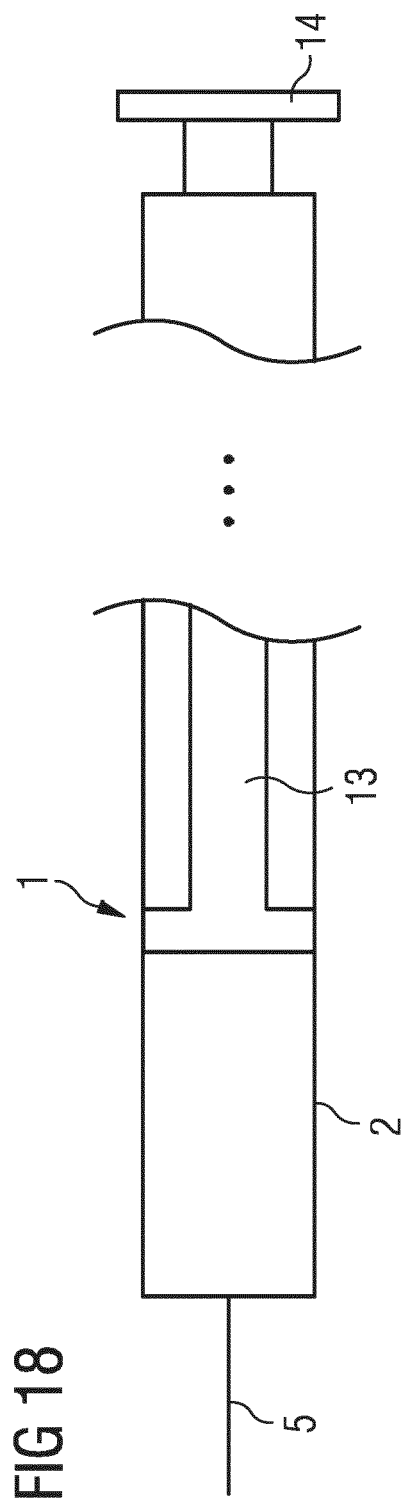
FIG. 18 schematically shows a sectional side view of parts of a medication delivery device according to a further embodiment.

FIG. 18 schematically shows a sectional side view of parts of a medication delivery device 1 according to an embodiment where the device 1 is a pre-filled syringe.

In this embodiment, the medication is directly retained in the body 2 without that a separate cartridge is provided. The body 2 may have a single-part design. Alternatively, the body 2 may have a multiple-part design. The further structural and functional elements may be configured as described for the embodiments of the foregoing figures.

What is claimed is:

1. An assembly for a medication delivery device, the assembly comprising:
    a body,
    a user operated dose setting part for selecting a size of a dose in a dose setting operation,
    a piston rod configured to be moved axially without rotating for dispensing a medication in a dose dispensing operation, and
    a drive member directly coupled to the piston rod for driving the piston rod in the dose dispensing operation,
    wherein the drive member moves in a proximal direction in the dose setting operation,
    wherein the dose setting part is coupled to the drive member such that a relative movement between the dose setting part and the drive member is enabled during the dose setting operation.

2. The assembly of claim 1, wherein the drive member protrudes out of the body in the dose setting operation.

3. The assembly of claim 1, wherein the drive member is configured to rotate and move in an axial direction in the dose setting operation.

4. The assembly of claim 1, wherein the piston rod is threadedly engaged with the drive member.

5. The assembly of claim 1, wherein the drive member is in splined connection with the dose setting part.

6. The assembly of claim 1, wherein the drive member, in the dose dispensing operation, is configured to axially move in a distal direction while being prevented from rotating, and wherein rotational movement of the drive member in the dose dispensing operation is prevented by an engagement part being engaged in an axial track of the body or of a component permanently locked to the body.

7. The assembly of claim 6, wherein the dose setting part comprises the engagement part.

8. The assembly of claim 6, wherein the drive member comprises the engagement part.

9. The assembly of claim 6, wherein the drive member or a component locked to the drive member comprises a prime-lock part, wherein the body or the component permanently locked to the body comprises a further prime-lock part, and wherein the prime-lock part and the further prime-lock part directly or indirectly interact with each other, thereby preventing the dose setting operation prior to a priming operation.

10. The assembly of claim 9, wherein the dose setting operation is carried out by rotating the dose setting part and the priming operation comprises pushing a dose dispense part towards the body.

11. The assembly of claim 9, wherein the prime-lock part is able to pass the further prime lock part or the engagement part in the dose setting operation.

12. The assembly of claim 11, wherein the drive member comprises a lock-out part and the body or the component permanently locked to the body comprises an additional lock-out part, wherein the lock-out part and the additional lock-out part interact after the dose has been set and dispensed for preventing a further dose setting operation after the dose has been dispensed.

13. The assembly of claim 12, wherein the additional lock-out part comprises a circumferential protrusion having an opening, wherein the lock-out part moves through the opening during the dose setting operation.

14. The assembly of claim 12, comprising a non-return member for preventing a proximal movement of the piston rod, wherein the non-return member comprises at least one of the additional lock-out part or a track for guiding the engagement part.

15. A medication delivery device comprising:
   an assembly having:
      a body,
      a user operated dose setting part for selecting a size of a dose in a dose setting operation,
      a piston rod configured to be moved axially without rotating for dispensing a medication in a dose dispensing operation, and
      a drive member directly coupled to the piston rod for driving the piston rod in the dose dispensing operation,
      wherein the drive member moves in a proximal direction in the dose setting operation,
   wherein the dose setting part is coupled to the drive member such that a relative
   movement between the dose setting part and the drive member is enabled during the dose setting operation, and
   wherein the medication delivery device is an injection device.

16. The medication delivery device of claim 15, wherein the injection device is a variable-dose, single-use device.

* * * * *